US008470243B2

(12) United States Patent
Nie et al.

(10) Patent No.: US 8,470,243 B2
(45) Date of Patent: Jun. 25, 2013

(54) SAMPLE PLATE FOR A BIOCHEMICAL ANALYZER

(75) Inventors: Baozhen Nie, Shenzhen (CN); Zaixing Gao, Shenzhen (CN); Leping Zhang, Shenzhen (CN); Ping Tian, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 41 days.

(21) Appl. No.: 13/051,817

(22) Filed: Mar. 18, 2011

(65) Prior Publication Data

US 2011/0256023 A1 Oct. 20, 2011

(30) Foreign Application Priority Data

Apr. 14, 2010 (CN) .......................... 2010 1 0153066

(51) Int. Cl.

| | |
|---|---|
| ***G01N 21/00*** | (2006.01) |
| ***G01N 31/00*** | (2006.01) |
| ***G01N 33/00*** | (2006.01) |
| ***G01N 35/00*** | (2006.01) |
| ***G01N 1/22*** | (2006.01) |

(52) U.S. Cl.

USPC ............... 422/64; 422/63; 436/45; 73/863.11

(58) Field of Classification Search

USPC ...................................................... 422/63–64

See application file for complete search history.

(56) References Cited

U.S. PATENT DOCUMENTS

| | | | | |
|---|---|---|---|---|
| 4,483,823 A | | 11/1984 | Umetsu et al. | |
| 4,774,055 A | * | 9/1988 | Wakatake et al. | 422/64 |
| 4,906,433 A | * | 3/1990 | Minekane | 422/64 |
| 5,051,238 A | * | 9/1991 | Umetsu et al. | 422/64 |
| 5,292,482 A | * | 3/1994 | Manabe | 422/64 |
| 5,885,529 A | * | 3/1999 | Babson et al. | 422/65 |

FOREIGN PATENT DOCUMENTS

| | | |
|---|---|---|
| CN | 1101547 A | 4/1993 |
| CN | 2862038 Y | 1/2007 |
| CN | 1963527 A | 5/2007 |
| CN | 201016986 Y | 2/2008 |
| CN | 101334416 A | 12/2008 |
| EP | 0289789 A1 | 9/1988 |
| EP | 1102068 A1 | 5/2001 |

* cited by examiner

*Primary Examiner* — Jill Warden

*Assistant Examiner* — Charles D Hammond

(74) *Attorney, Agent, or Firm* — Kory D. Christensen; Stoel Rives LLP

(57) ABSTRACT

A sample plate for a biochemical analyzer is provided, which includes a main shaft, an inner plate, an outer plate, a refrigeration bin, a tubing portion, a cooling fluid inlet and a cooling fluid outlet.

10 Claims, 4 Drawing Sheets

SAMPLE PLATE FOR A BIOCHEMICAL ANALYZER

CROSS-REFERENCE TO RELATED APPLICATIONS

This application claims the benefit of Chinese Patent Application No. 201010153066.6, filed Apr. 14, 2010, which is incorporated herein by reference in its entirety.

TECHNICAL FIELD

The following disclosure relates to biochemical analyzers.

SUMMARY OF THE INVENTION

A sample plate for a biochemical analyzer is disclosed.

DETAILED DESCRIPTION

Figure 1:
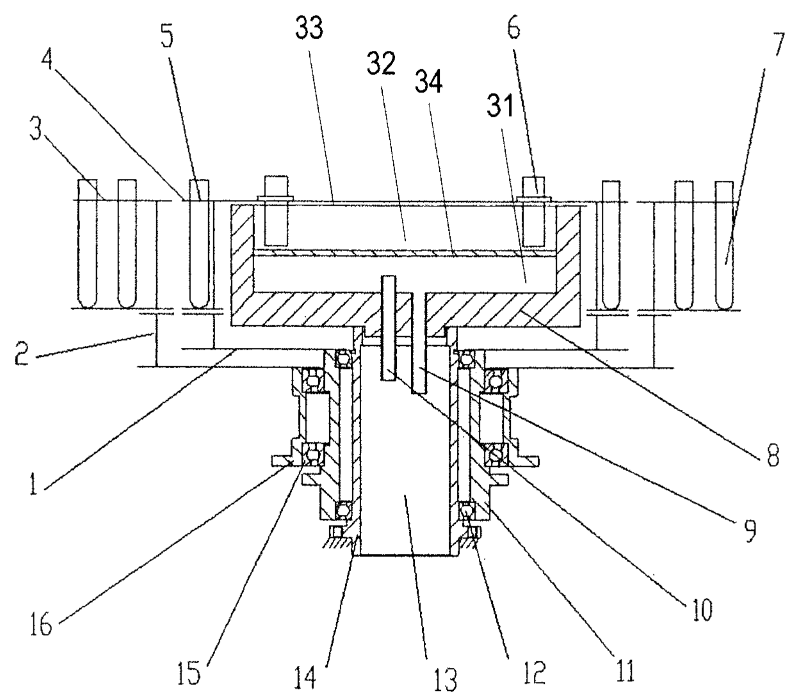
FIG. 1 is a sectional view of a sample plate for a biochemical analyzer.

A biochemical analyzer usually includes a sample plate for placing a sample. Current sample plates generally have two functional demands:

1. sample plate refrigeration, since part of the samples (such as a quality control sample) needs cold storage; the part of the samples on the sample plate needs a refrigeration function;

2. independent rotation of inner and outer plates: in order to improve testing efficiency of the sample, the sample plate needs to have an inner plate and an outer plate that rotate independently; when one plate body rotates and tests, the other plate body may stop rotating and perform a sample replacement operation, so as to make sure that the sample plate is always at a testing state, thereby improving the testing efficiency.

Currently, there is no good approach for simultaneously realizing the independent rotation function of the inner and outer plates and the refrigeration function. Existing solutions realize the functions through two entirely independent structures. Consequently, not only the machine cost is increased, but also the structures occupy a larger volume, making the entire instrument awkward.

According to one embodiment, a sample plate for a biochemical analyzer is provided, which includes a main shaft, an inner plate, an outer plate, a refrigeration bin, a tubing portion, a cooling fluid inlet and a cooling fluid outlet. The main shaft may be fixed on the biochemical analyzer. The inner plate may be installed on the main shaft for rotating independent of the outer plate. The outer plate may be installed on the main shaft for rotating independently of the inner plate. The inner plate may include an inner plate body for placing a sample. The inner plate body may include an inner ring part for placing the sample. The outer plate may include an outer plate body for placing the sample. One end of the cooling fluid inlet and one end of the cooling fluid outlet may be connected to the refrigeration bin, and the other end of the cooling fluid inlet and the other end of the cooling fluid outlet may be connected to the tubing portion. The tubing portion may be used for providing a tubing space for the refrigeration bin. The sample placed in the inner ring part may be disposed in the refrigeration bin.

In one embodiment, the inner plate further includes an inner plate bearing and an inner plate bearing sleeve. The inner plate bearing may be connected to the main shaft; the inner plate bearing sleeve may be connected to the inner plate bearing; and the inner plate body may be connected to the inner plate bearing sleeve.

The outer plate may further include an outer plate bearing and an outer plate bearing sleeve. The outer plate bearing may be connected to the inner plate bearing sleeve; the outer plate bearing sleeve may be connected to the outer plate bearing; and the outer plate body may be connected to the outer plate bearing sleeve.

In one embodiment, the main shaft is a hollow shaft, and a hollow part of the hollow shaft is the tubing portion. The inner plate may further include an inner plate bearing and an inner plate bearing sleeve; the inner plate bearing may be connected to the main shaft; the inner plate bearing sleeve may be connected to the inner plate bearing; and the inner plate body may be connected to the inner plate bearing sleeve.

The outer plate may further include an outer plate bearing and an outer plate bearing sleeve. The outer plate bearing may be connected to the main shaft. The outer plate bearing sleeve may be connected to the outer plate bearing. The outer plate body may be connected to the outer plate bearing sleeve.

In one embodiment, the main shaft is a hollow shaft, and a hollow part of the hollow shaft is the tubing portion. The main shaft may include a first main shaft and a second main shaft. The inner plate may further include an inner plate bearing and an inner plate bearing sleeve. The inner plate bearing may be connected to the first main shaft. The inner plate bearing sleeve may be connected to the inner plate bearing. The inner plate body may be connected to the inner plate bearing sleeve.

The outer plate may further include an outer plate bearing and an outer plate bearing sleeve. The outer plate bearing may be connected to the second main shaft. The outer plate bearing sleeve may be connected to the outer plate bearing. The outer plate body may be connected to the outer plate bearing sleeve.

In one embodiment, the second main shaft is a hollow shaft. A hollow part of the hollow shaft may partially accommodate the inner plate bearing, the inner plate bearing sleeve, and the first main shaft, and the rest hollow part may be the tubing portion.

In one embodiment, the refrigeration bin includes a cooling fluid bin and a sample bin. The cooling fluid bin and the sample bin may be independent from each other and may be separated by a baffle. In one configuration, the cooling fluid bin is used for placing cooling fluid, and the sample bin is used for placing the sample.

The refrigeration bin may further include a refrigeration bin cap disposed on the refrigeration bin, which may be used for reducing heat transfer between the refrigeration bin and a surrounding space.

The inner plate may further include an outer ring part for placing the sample, and the outer ring part may be disposed outside the refrigeration bin.

Figure 2:
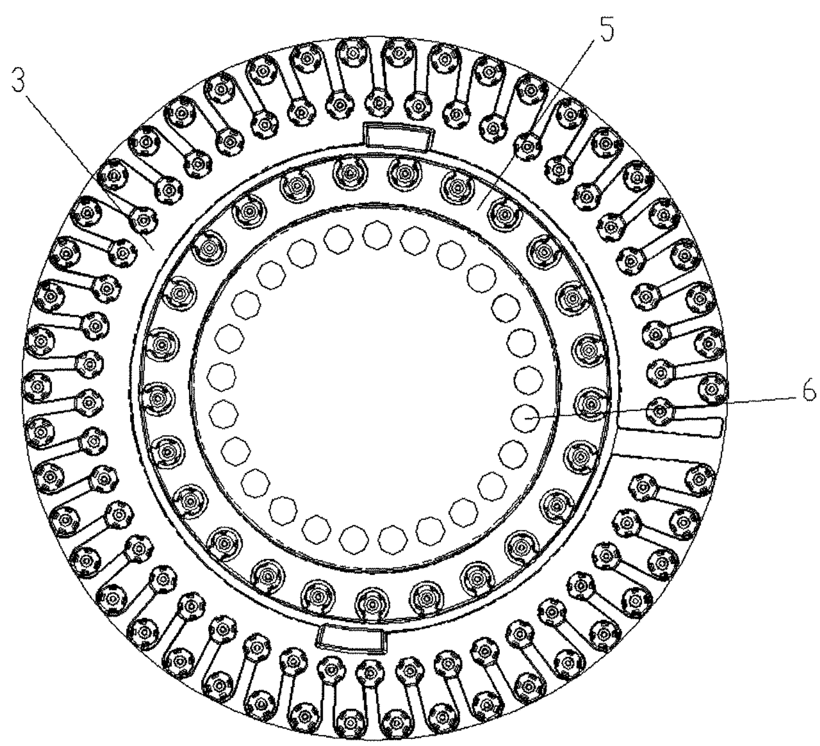
FIG. 2 is a top view of a sample plate for the biochemical analyzer.
Figure 3:
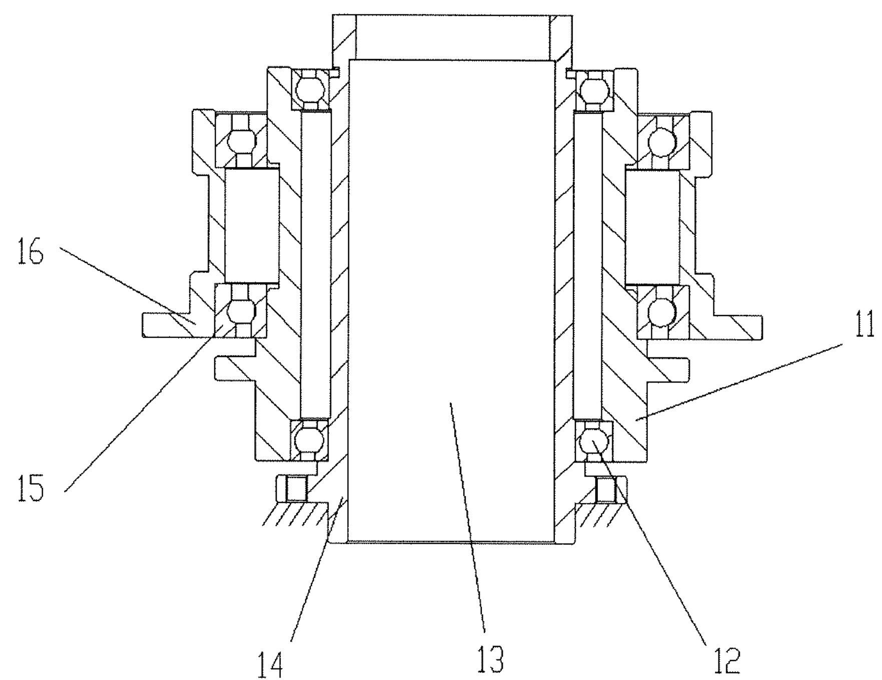
FIG. 3 is an amplified view of a slewing mechanism of the sample plate for the biochemical analyzer.

FIG. 1, FIG. 2, and FIG. 3 are schematic structural views of an embodiment of a sample plate for a biochemical analyzer. The embodiment will be described in detail below with reference to the accompanying drawings.

A sample plate may include an outer plate part and an inner plate part. The outer plate part may includes an outer plate slewing mechanism 2 and an outer plate body 3, and the inner plate part may include an inner plate slewing mechanism 1 and an inner plate body 4.

In one embodiment, the slewing mechanisms have two suites of bearings, namely, an inner plate bearing 12 and an outer plate bearing 15. The two suites of bearings may be coaxial bearings, and the two suites of bearings may be integrated into one. A fixing main shaft 14 may be fixed, and may be a hollow shaft. Rotation of the inner plate bearing 12 may drive the inner plate bearing sleeve 11 to rotate, thereby driving the inner plate slewing mechanism 1 and the inner plate part to rotate. The outer plate baring 15 may be connected to the inner plate bearing sleeve 11. Rotation of the outer plate bearing 15 may drive the outer plate bearing sleeve 16 to rotate, thereby driving the outer plate slewing mechanism 2 and the entire outer plate part to rotate. In this manner, the independent rotation of the inner and outer plates can be realized.

An inner plate inner ring part 6 may used to realize the refrigeration function, and the outer plate body 3 and an inner plate outer ring part 5 do not have the refrigeration function in one embodiment. The main shaft 14 in the most internal level of the slewing mechanisms may be fixed. A refrigeration bin 8 may be fixed on the main shaft 14. The main shaft 14 may be a hollow structure, and the hollow structure may form a tubing portion. The tubing of a cooling fluid inlet 9 and a cooling fluid outlet 10 in a refrigeration part can be performed through a middle cavity 13 of the main shaft 14, therefore realizing the refrigeration function. In one embodiment, the refrigeration bin 8 is divided into a cooling fluid bin 31 and a sample bin 32. The cooling fluid bin 31 and the sample bin 32 may be independent from each other and separated by a baffle 34. The cooling fluid bin 31 may be used for placing cooling fluid, and the sample bin 32 may be used for placing the sample.

In one embodiment, the outer plate body 3 is an integral part, and, in fact, can be divided into multiple rings of structures capable of rotating independently. Referring to FIG. 1, the outer plate body 3 may include two rings of sample containers 7, and the two rings of sample containers 7 may be distributed on a same plate body and can rotate simultaneously. The outer plate body 3 may also employ two levels of coaxial structures that rotate independently to drive the two rings of sample containers 7, and in this manner, the independent rotation of the two rings of sample containers can be realized. Similarly, the independent rotation of multiple rings of sample containers 7 can be realized.

The inner plate body 4 may be divided into the outer ring part 5 and the inner ring part 6, and the two parts may be distributed on a same plate surface and share a same slewing mechanism. A part where the inner plate body 4 and the inner plate slewing mechanism 1 are directly connected is the outer ring part. In one embodiment, when the inner plate slewing mechanism 1 drives the inner plate body to rotate, the outer ring part 5 and the inner ring part 6 of the inner plate rotate at the same time. In this manner, a middle part of the structure can leave an enough space for the inner ring part 6 of the inner plate to realize the refrigeration function.

In one embodiment, the slewing mechanisms of the inner and outer plates are coaxial and may rotate independently, in which the main shaft 14 of the most internal level of the slewing mechanisms is fixed, and is a hollow shaft. The main shaft 14 may provide a support and tubing space for the refrigeration part. In this manner, two major functions required by the sample plate, that is, the independent rotation function of the inner and outer plates and the refrigeration function, can be achieved in the same structure.

In one embodiment of a sample plate for a biochemical analyzer, an outer plate bearing is connected to an inner plate bearing sleeve. In fact, as for a connection position of the outer plate bearing, at least two substitution solutions exist.

1. The outer plate bearing is connected to the main shaft.

Figure 4:
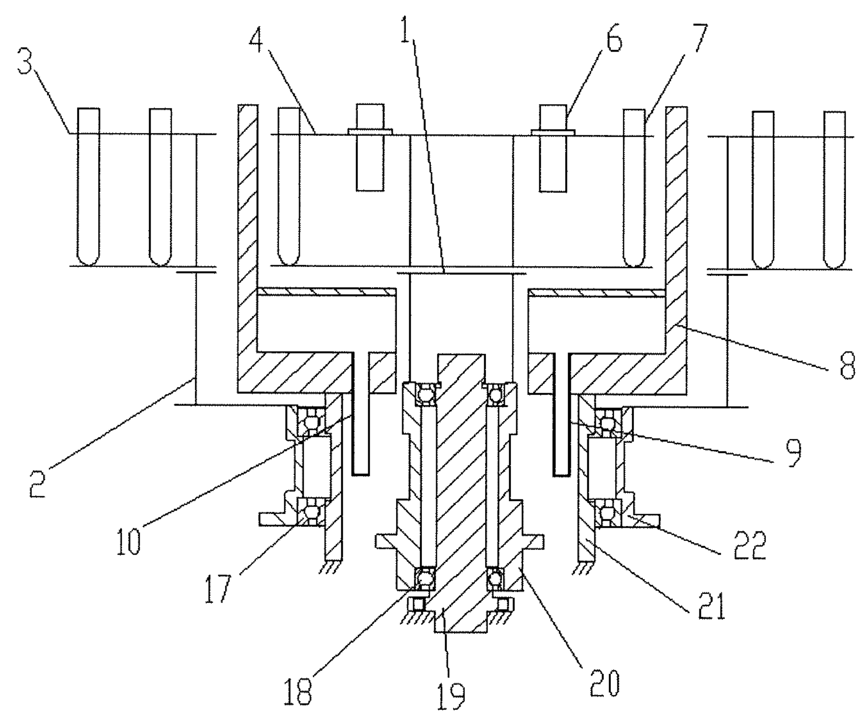
FIG. 4 is a schematic sectional view of an outer plate bearing connection position of the sample plate for the biochemical analyzer.

2. As shown in FIG. 4, an inner plate bearing 18 may be connected to an inner plate fixing shaft 19. An inner plate bearing sleeve 20 may be connected to the inner plate bearing 18. An inner plate body 4 may be connected to the inner plate bearing sleeve 20. An outer plate bearing 17 may be connected to an outer plate fixing shaft 21. An outer plate bearing shaft 22 may be connected to the outer plate baring 17. An outer plate body 3 may be connected to the outer plate bearing sleeve 22, in which the inner plate fixing shaft 19 may be hollow or solid. The outer plate fixing shaft 21 may be hollow, in which a hollow part is used for accommodating the inner plate fixing shaft 19, the inner plate bearing 18, the inner plate bearing sleeve 20 and a refrigeration bin 8, and further providing the tubing or support for realizing the refrigeration part, which is the same as tubing portion. As illustrated, the refrigeration bin 8 may be disposed in the hollow part, and samples 6 and 7 on the inner plate body 4 may be disposed in the refrigeration bin. A cooling fluid inlet 9 and a cooling fluid outlet 10 may be disposed in the hollow part (that is, the tubing portion). By employing such a structure, the refrigeration can be realized, and the independent rotation of the inner and outer plates is not affected.

Based on the foregoing embodiment, the following changes may be implemented:

1. increasing the number of the plate bodies, that is, increasing the number of the plate bodies to three or more, in which each plate body corresponds to a level of slewing mechanism, thus realizing the independent rotation of multiple levels of plate bodies;

2. dividing the inner plate into multiple rings, so as to realize the refrigeration of the multiple rings of the samples, in which each ring of the inner plate may employ one level of slewing mechanism, thus realizing the refrigeration and independent rotation of the multiple rings;

3. the inner plate only having the inner ring for placing the sample;

4. adding a movable refrigeration bin cap 33 on the refrigeration bin 8, in which the refrigeration bin cap 33 does not affect the rotation and usage of the sample plate, and can effectively increase a refrigerant efficiency, prevent heat transfer and save energy; when an operation needs to be performed on the sample on the inner ring, it is only needed to remove a sealing cap 33.

Although the present disclosure has been described with reference to the specific embodiments, such embodiments are not intended to limit the present disclosure. Those of skill in the art can make modifications and variations without departing from the spirit and scope of the present disclosure.

What is claimed is:

1. A sample plate for a biochemical analyzer comprising:

a main shaft;

an inner plate;

an outer plate;

a refrigeration bin;

a tubing portion;

a cooling fluid inlet; and a cooling fluid outlet;

wherein the main shaft is fixed on the biochemical analyzer;

wherein the inner plate is installed on the main shaft for rotating independent of the outer plate;

wherein the outer plate is installed on the main shaft for rotating independent of the inner plate;

wherein the inner plate comprises an inner plate body for placing a sample;

wherein the inner plate body comprises an inner ring part for placing the sample;

wherein the outer plate comprises an outer plate body for placing the sample;

wherein one end of the cooling fluid inlet and one end of the cooling fluid outlet are connected to the refrigeration bin, and the other end of the cooling fluid inlet and the other end of the cooling fluid outlet are connected to the tubing portion;

wherein the tubing portion is used for providing a tubing space for the refrigeration bin;

wherein the sample placed in the inner ring part is disposed in the refrigeration bin; and wherein the main shaft is a hollow shaft, and a hollow part of the hollow shaft is the tubing portion.

2. The sample plate for the biochemical analyzer according to claim 1, wherein the inner plate further comprises an inner plate bearing and an inner plate bearing sleeve; the inner plate bearing is connected to the main shaft; the inner plate bearing sleeve is connected to the inner plate bearing; the inner plate body is connected to the inner plate bearing sleeve; and wherein the outer plate further comprises an outer plate bearing and an outer plate bearing sleeve; the outer plate bearing is connected to the inner plate bearing sleeve; the outer plate bearing sleeve is connected to the outer plate bearing; the outer plate body is connected to the outer plate bearing sleeve.

3. The sample plate for the biochemical analyzer according to claim 1, wherein the inner plate further comprises an inner plate bearing and an inner plate bearing sleeve; the inner plate bearing is connected to the main shaft; the inner plate bearing sleeve is connected to the inner plate bearing; the inner plate body is connected to the inner plate bearing sleeve; and wherein the outer plate further comprises an outer plate bearing and an outer plate bearing sleeve; the outer plate bearing is connected to the main shaft; the outer plate bearing sleeve is connected to the outer plate bearing; the outer plate body is connected to the outer plate bearing sleeve.

4. The sample plate for the biochemical analyzer according to claim 1, wherein the main shaft comprises an inner plate fixing shaft and an outer plate fixing shaft;

wherein the inner plate further comprises an inner plate bearing and an inner plate bearing sleeve; the inner plate bearing is connected to the inner plate fixing shaft; the inner plate bearing sleeve is connected to the inner plate bearing; the inner plate body is connected to the inner plate bearing sleeve;

wherein the outer plate further comprises an outer plate bearing and an outer plate bearing sleeve; the outer plate bearing is connected to the outer plate fixing shaft; the outer plate bearing sleeve is connected to the outer plate bearing; the outer plate body is connected to the outer plate bearing sleeve; and wherein the outer plate fixing shaft is a hollow shaft configured to at least partially accommodate the inner plate bearing, the inner plate bearing sleeve and the inner plate fixing shaft.

5. The sample plate for the biochemical analyzer according to claim 1, wherein the refrigeration bin comprises a cooling fluid bin and a sample bin; the cooling fluid bin and the sample bin are independent from each other and separated by a baffle; the cooling fluid bin is used for placing cooling fluid, and the sample bin is used for placing the sample.

6. The sample plate for the biochemical analyzer according to claim 1, further comprising:

a refrigeration bin cap disposed on the refrigeration bin, wherein the refrigeration bin cap is used for reducing heat transfer between the refrigeration bin and a surrounding space.

7. The sample plate for the biochemical analyzer according to claim 1, wherein the inner plate further comprises an outer ring part for placing the sample, and the outer ring part is disposed outside the refrigeration bin.

8. The sample plate for the biochemical analyzer according to claim 1, further comprising a ring of sample containers placed on the inner ring part.

9. The sample plate for the biochemical analyzer according to claim 1, further comprising a ring of sample containers placed on the outer plate body.

10. The sample plate for the biochemical analyzer according to claim 1, wherein the outer plate comprises a plurality of rings, wherein each ring is installed on the main shaft and configured to rotate independent of other rings.

* * * * *